United States Patent [19]

Wang et al.

[11] Patent Number: 5,932,205
[45] Date of Patent: Aug. 3, 1999

[54] BIOCHEMICAL CONTACT LENS FOR TREATING PHOTOABLATED CORNEAL TISSUE

[76] Inventors: Ming X. Wang, 2000 Grand Ave. #406, Nashville, Tenn. 37212; Christopher P. Adams, 255 Broadway, Winter Hill, Mass. 02145

[21] Appl. No.: 08/899,783

[22] Filed: Jul. 24, 1997

[51] Int. Cl.$^6$ .......................... A61K 31/74; A61K 47/30
[52] U.S. Cl. ...................... 424/78.04; 514/772.3
[58] Field of Search ....................... 424/78.04; 514/772.3

[56] References Cited

U.S. PATENT DOCUMENTS

| | | | |
|---|---|---|---|
| 4,648,400 | 3/1987 | Schneider, et al. | 128/303.1 |
| 4,665,913 | 5/1987 | L'Esperance, Jr. | 128/303.1 |
| 4,669,466 | 6/1987 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,973,466 | 11/1990 | Reich | 424/426 |
| 4,973,493 | 11/1990 | Guire | 427/2 |
| 5,023,114 | 6/1991 | Halpern et al. | 427/338 |
| 5,163,934 | 11/1992 | Munnerlyn | 606/5 |
| 5,604,200 | 2/1997 | Taylor-McCord | 514/8 |

OTHER PUBLICATIONS

Trokel, S.L., et al., "Excimer Laser Surgery of the Cornea", *American Journal of Ophthalmology*, 96:710–715 (1983).

Fantes, F.E., et al., "Wound Healing After Excimer Laser Keratomileusis (Photorefractive Keratectomy) in Monkeys", *Arch Ophthal*, 108:665–675 (1990).

Hanna K.D., et al., "Corneal Stromal Wound Healing in Rabbits After 193–nm Excimer Laser Surface Ablation", *Arch Opthal*, 107:895–901 (1989).

Holme, R.J., et al., "A Comparison of En Face and Tangential Wide–Area Excimer Surface Ablation in the Rabbit", *Arch Ophthal*, 108:876–881 (1990).

Taylor, D.M., et al., "Human Excimer Laser Lamellar Keratectomy, A Clinical Study", *Opthal*, 96:654–664 (1989).

O'Brat D., et al., "The Effects of Topical Corticosteroids and Plasmin Inhibitors on Refractive Outcome, Haze, and Visual Performance after Photorefractive Keratectomy", *Opthal*, 101:1565–1574 (1994).

Gartry, D.S. et al., "The Effect of Topical Corticosteroids on Refraction and Corneal Haze Following Excimer Laser Treatment of Myopia: An Update. A Prospective Randomised, Double–Masked Study", *Eye*, 7:584–590 (1993).

Bergman, R.H., et al., "The Role of Fibroblast Inhibitors on Corneal Healing Following Photorefractive Keratectomy with 193–Nanometer Excimer Laser in Rabbits", *Ophthal Surg*, 25(3):170–174 (1994).

Talamo, J.H., et al., "Modulation of Corneal Would Healing After Excimer Laser Keratomileusis Using Topical Mitomycin C and Steroids", *Arch Ophthal*, 109(8):1141–1146 (1991).

Rieck, P., et al., "Basic fibroblast growth factor modulates corneal wound healing after excimer laser keratomileusis in rabbits", *German J Ophthal*, 3:105–111 (1994).

Morlet, N., et al., "Effect of Topical Interferon–Alpha 2b on Corneal Haze After Excimer Laser Phtorefractive Kratectomy in Rbbits", *Refrac. Corneal Surg*, 9(6):443–451 (1993).

Filipec, M., et al., "Topical Cyclosporine A and Corneal Wound Healing", *Cornea*, 11(6):546–552 (1992).

Mastubara, M., et al., "The Effect of Active Vitamin D to the Wound Healing After Excimer laser Phototherapeutic Keratectomy (PTK)", *Inves. Ophth. Visci.*, (37):S198 (1996).

Niizuma, T., et al., "Cooling the Cornea to Prevent Side Effects of Photorefractive Keratectomy", *Suppl. to J. Refract. & Corneal Surg.*, 10:S262–S266 (1994).

Rawe, I.M., et al., "A Morphological Study of Rabbit Corneas After Laser Keratectomy", *Eye*, 6:637–642 (1992).

Wu, Wilson C.S., et al., "Corneal Wound Healing After 193–nm Excimer Laser Keratectomy", *Arch Ophthalmol*, 109:1426–1432 (1991).

Streuli, C.H., et al., "Extracellular Matrix Regulates Expression of the TGF–$\beta$1 Gene", *J Cell Biology*, 120:253–260 (1993).

Shah, M., et al., "Neutralisation of TGF–$\beta_1$ and TGF–$\beta_2$ or exogenous addition of TGF–$\beta_3$ to cutaneous rat wounds reduces scarring" *J of Cell Science*, 108:985–1002 (1995).

Gimbel, Howard V., et al., "Effect of Contact Lens Wear on Photorefractive Keratectomy", *the CLAO Journal*, 19:217–221 (1993).

*Primary Examiner*—Carlos Azpuru
*Attorney, Agent, or Firm*—Giulio A. DeConti, Jr.; Lahive & Cockfield LLP

[57] ABSTRACT

Methods for treating photoablated corneal tissue are described. The methods include contacting photoablated corneal tissue with a contact lens which includes an amniotic composition such that scarring of the photoablated corneal tissue is reduced. Methods for conditioning a contact lens for treatment of photoablated corneal tissue are also described. The methods include contacting the contact lens with an amniotic composition whereby the amniotic composition is deposited in or on the surface of said contact lens. Additionally, contact lens packages for treatment of photoablated corneal tissue are described. The contact lens package includes a container holding a contact lens which includes an amniotic composition and instructions for using the contact lens for treatment of photoablated corneal tissue.

14 Claims, No Drawings

BIOCHEMICAL CONTACT LENS FOR TREATING PHOTOABLATED CORNEAL TISSUE

BACKGROUND

The human eye is an extremely powerful focusing device that produces an image on the surface of the retina. The focusing elements of the eye are the cornea and the lens. The cornea accounts for approximately 80 percent of the focusing ability (48 diopters) and the lens approximately 20 percent (12 diopters). In the case of myopia, the eye is assumed to have a longer egg-like shape in which case the light beam focuses to a spot located in front of the retina and therefore is out of focus. In hyperopia, the focusing system is inadequate, and the focusing spot and image are located behind the retina and also out of focus. In the case of astigmatism, a spot or clear image is not created, and the eye basically focuses at two areas behind or in front of the retinal surface. In order to correct myopia, hyperopia, or astigmatism, spectacles or contact lenses are used to place the image directly on the rods and cones of the retina.

The cornea is a thin shell with nearly concentric anterior and posterior surfaces and a central thickness of about 520 micrometers. It has an index of refraction of 1.377 and a nominal radius of curvature of 7.86 mm. The epithelium, forming the anterior surface of the cornea, is about 50 micrometers thick. The epithelial cells are capable of very rapid regrowth, and it is known that the epithelium can be removed from the cornea and will quickly regrow to resurface the area from which it was removed. Underlying the epithelium is a layer called Bowman's layer or Bowman's membrane, which is about 20 micrometers thick. This covers the anterior surface of the stroma, which makes up the bulk of the cornea and consists primarily of collagen fibers. The endothelium, forming the posterior layer of the cornea, is a single layer of cells that do not reproduce.

About three-quarters of the refractive power of the eye is determined by the curvature of the anterior surface of the cornea, so that changing the shape of the cornea offers a way to significantly reduce or eliminate a refractive error of the eye. Since the epithelium readily regrows, a change in the shape of the anterior surface of the cornea must be made by modifying Bowman's layer and the stroma to be permanent. The stroma is thick enough so that portions of its anterior region can be ablated away to change its profile and thus change the refractive power of the eye for corrective purposes, while leaving plenty of remaining stroma tissue. For example, a change of 5 diopters requires only 27 microns of stromal removal within a 4 mm diameter region.

As discovered by Stephen L. Trokel ("Excimer Laser Surgery of the Cornea", *American Journal of Ophthalmology*, December 1983), far ultraviolet radiation from an excimer laser can be used to change the refractive power of the cornea of an eye. The radiation ablates away corneal tissue in a photodecomposition that does not cause thermal damage to adjacent tissue, and can be called photorefractive keratectomy (PRK). A similar photodecomposition of corneal tissue can be achieved with an infrared laser operating near 2.9 micrometers, where thermal damage to adjacent tissue is minimized by the high absorption of water.

L'Esperance U.S. Pat. No. 4,665,913 describes procedures for changing the contour of the anterior surface of the cornea of the eye by directing pulses from an excimer laser in a scanning pattern that moves around the cornea. The laser pulses first ablate and remove the epithelium of the cornea, and then the ablation penetrates into the stroma of the cornea to change its contour for various purposes, such as correcting myopia or hyperopia. Schneider et al. U.S. Pat. No. 4,648,400 suggests radial keratectomy with an excimer laser that also ablates away the epithelium before penetrating into and changing the contour of, the stroma of the cornea.

Ultraviolet laser based systems and methods which are known for enabling ophthalmological surgery on the surface of the cornea in order to correct vision defects by the technique known as ablative photodecomposition. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference. U.S. Pat. No. 4,665,913 issued May 19, 1987 for "METHOD FOR OPHTHALMOLOGICAL SURGERY"; U.S. Pat. No. 4,669,466 issued Jan. 2, 1987 for "METHOD AND APPARATUS FOR ANALYSIS AND CORRECTION OF ABNORMAL REFRACTIVE ERRORS OF THE EYE"; U.S. Pat. No. 4,732,148 issued Mar. 22, 1988 for "METHOD FOR PERFORMING OPHTHALMIC LASER SURGERY"; U.S. Pat. No. 4,770,172 issued Sep. 13, 1988 for "METHOD OF LASER-SCULPTURE OF THE OPTICALLY USED PORTION OF THE CORNEA"; U.S. Pat. No. 4,773,414 issued Sep. 27, 1988 for "METHOD OF LASER-SCULPTURE OF THE OPTICALLY USED PORTION OF THE CORNEA"; U.S. patent application Ser. No. 109,812 filed Oct. 16, 1987 for "LASER SURGERY METHOD AND APPARATUS"; and U.S. Pat. No. 5,163,9034 issued Nov. 17, 1992 for "PHOTOREFRACTIVE KERATECTOMY".

In the above-cited U.S. Pat. No. 4,665,913 several different techniques are described which are designed to effect corrections for specific types of optical errors in the eye. For example, a myopic condition is corrected by laser sculpting the anterior corneal surface to reduce the curvature. In addition, a stigmatic condition, which is typically characterized by a cylindrical component of curvature departing from the otherwise generally spherical curvature of the surface of the cornea, is corrected by effecting cylindrical ablation about the axis of cylindrical curvature of the eye. Further, a hyperopic condition is corrected by laser sculpting the corneal surface to increase the curvature.

In a typical laser surgical procedure, the region of the anterior corneal surface to be ablated in order to effect the optical correction is designated the optical zone. Depending on the nature of the desired optical correction, this zone may or may not be centered on the center of the pupil or on the apex of the anterior corneal surface.

A majority of patients develop various degrees of corneal haze following excimer photorefractive keratectomy (PRK) (Lohmann C, Gartry D, Kerr Muir M, et al. "Haze in Photorefractive Keratectomy: Its origins and consequences," Lasers and Light in Ophthal. 1991, 4, 15–34; Fante F E, Hanna K D, Waring G O, et al. "Wound healing after excimer laser keratomileusis (photorefractive keratectomy) in monkeys," Arch. Ophthal. 1990, 108:665–675). Corneal haze typically peaks at two to four months and has been noted to increase with the degree of myopia corrected (e.g., 2+ stable haze defined according to the standard haze grading scale described by Fante et al., supra., occurs in 11% of patients with corrections greater than eight diopters. Such haze can lead to the loss of one or more lines of best corrected visual acuity after PRK. Corneal stromal remodeling influences the degree of corneal haze after PRK and is believed to be responsible for a reduction in the best possible corrected visual acuity, regression for refractive correction and poor predictability for the attempted correction.

The formation of the corneal haze after PRK is a result of laser corneal ablation and stromal wound healing. Despite significant advances made in understanding PRK technology (e.g., laser-tissue interaction, optical profiling of the laser beam, multi-zone multi-pass approaches and edge-smoothing techniques), characterization of biological aspects associated with PRK, such as wound healing, remains a significant limitation associated with PRK technology (Fante F E, Hanna K D, Waring G O, et al., "Wound healing after excimer laser keratomileusis (photorefractive keratectomy) in monkeys," Arch. Ophthal. 1990, 108:665–675; Hanna K D, Pouliquen Y, Waring G O, et al., "Corneal stromal wound healing in rabbits after 193-nm excimer laser surface ablation," Arch. Ophthal. 1989, 107:895–901; Holm R J, Fouraker B D, Schanzlin D J. "A comparison of a face and tangential wide-area excimer surface ablation in rabbits," Arch. Ophthal. 1990, 108:876–881; Taylor D M, L'Esperance F A, Del Pera R A, et al., "Human excimer laser lamellar keratectomy, A clinical study," Opthal. 1989, 96:654–664; Marshal J, Trokel S, Rothery S, et al., "Photoablative reprofiling of the cornea using an excimer laser: photorefractive keratectomy," Lasers in Ophthal. 1986, 1:21–48; Tuft S, Marshall J, Rothery S. "Stromal remodeling following photorefractive keratectomy," Lasers Ophthal. 1987, 1:177–183). Treatments to reduce corneal haze after PRK have not been proven effective (O'Brat D, Lohmann C P, Klonos G, Corbett M C, Pollock W, Ker-Muir M G and Marshall J., "The effects of topical corticosteroids and plasmin inhibitors on refractive outcome, haze, and visual performance after photorefractive keratectomy," Ophthal. 1994, 101:1565–1574; Gartry, D S, Kerr Muir M G, and Marshall, J, "The effect of topical corticosteroids on refraction and corneal haze following excimer laser treatment of myopia: An update up a Prospective, randomized, double-masked study," Eye 1993, 7:584–590; Bergman R H, Spidelman A V, "The role of fibroblast inhibitors on corneal healing following photorefractive keratectomy with 193-nm excimer laser in rabbits," Ophthal Surg. 1994, 25(3):170–174; Talma J H, Gallamudi S, Green W R, De La Cruz Z, Filatov V, Stark W J., "Modulation of corneal wound healing after excimer laser keratomileusis using topical mitomycin C and steroids," Arch. Ophthal. 1991, 109(8):1141–1146; Rieck P, David T, Hartman C, Renard G, Courtois Y and Pouliquen Y., "Basic fibroblast growth factor modulates corneal wound healing after excimer laser keratomileusis in rabbits," German J. Ophthal. 1994, 3:105–111; Morlet N, Gillies M C, Grouch R, Mallof A., "Effect of topical interferon-alpha 2b on corneal haze after excimer laser photorefractive keratectomy in rabbits," Refrac. Corneal Surg. 1993, 9(6):443–451; Filipec M, MaiPhan T, Zhao T-Z, Rice B A, Merchant A, and Foster C. Cornea, 1992, 11(6):546–552; Mastubara M, Sasaki A, Ita S., "The effect of active vitamin D to the wound healing after excimer laser phototherapeutic keratectomy (PTK)," ARVO, 1996, 37(3):S198; Niizuma T, Ito S, Hayashi M Futemma M, Utsumi T, Ohashi K., "Cooling the cornea to prevent side effects of photorefractive keratectomy," Suppl. to J. Refract. & Corneal Surg. 1994, 10:S262–S266).

These various treatments for reducing corneal haze after excimer laser ablation have met with limited success. For example, the use of topical steroids has been found to be ineffective for the reduction of corneal haze. With regard to refractive outcome, though corticosteroids can maintain a hyperopic shift during their administration. However, the effect is reversed upon cessation of treatment. Consequently, there appears to be no justification for subjecting patients to long-term treatment with steroids for corneal haze in view of adverse side effects associated with steroidal treatments.

Other pharmacological treatments have also not been found to decrease post PRK haze. These treatments have included the use of plasmin inhibitors, fibroblast inhibitors, mitomycin, fibroblast growth factor, interferon-alpha 2b, cyclosporin A, active forms of vitamin D, as well as cooling of corneal surface (Rawe I M, Zabel R W, Tuft S J, Chen V and Meek K M., "A morphological study of rabbit corneas after laser keratectomy," Eye 1992, 6:637–642; Wu W C S, Stark W J and Green W R., "Corneal wound healing after 192-nm excimer laser keratectomy,: Arch. Ophthalmol. 1991, 109:1426–1432).

SUMMARY OF THE INVENTION

The present invention is based, at least in part, on the discovery that contact lenses which are treated with an amniotic composition derived from amniotic membrane can be used to treat corneal tissue after photoablation, e.g., PRK, to reduce corneal scarring. The present invention provides a method for treating photoablated corneal tissue. The method includes contacting photoablated corneal tissue with a contact lens. The contact lens includes an amniotic composition such that scarring of the photoablated corneal tissue is reduced. Typical contact lens materials include those formed from polymethylmethacrylate, polysiliconeacrylates, polysiliconemethacrylates, polyfluoroacrylates, polyfluoromethacrylates, polyflurosiliconeacrylates, polysiliconemethacrylates, polymethacrylates, polyacrylates, or polyitaconates, polyurethanes, polysiliconeurethanes and combinations thereof.

The present invention also provides a method for conditioning a contact lens for treatment of photoablated corneal tissue. The method includes contacting the contact lens with an amniotic composition whereby the amniotic composition is deposited within the contact lens or is deposited on the surface of the contact lens. Suitable amniotic compositions include extracts from amniotic tissue and placental components.

The present invention also provides a contact lens packaged as a kit for treatment of photoablated corneal tissue. The kit includes a container for holding a contact lens which includes an amniotic composition and instructions for using the contact lens for treatment of photoablated corneal tissue. Scarring of the photoablated corneal tissue is reduced by the amniotic composition.

This invention provides several advantages over known methods employed for reducing corneal haze. For example, the method provides a contact lens which acts as a support for typically fragile amniotic membranes or films which could otherwise disintegrate, tear or adhere to the corneal tissue. Further, the use of a contact lens as a support eliminates the potential need for suturing of an amniotic composition to photoablated corneal tissue. In addition, the contact lens which includes an amniotic composition can be readily removed and manipulated, thereby allowing an individual to change the lens as needed. Also, the invention provides amniotic compositions entrapped within a contact lens, such that tissue repair factors can diffuse to the photoablated corneal tissue. The lens can be treated on a periodic basis with a solution containing an amniotic composition having tissue repair and growth factors, such that diffusion of these factors from the contact lens can be maintained at optimal levels.

DETAILED DESCRIPTION

The features and other details of the invention will now be more particularly described and pointed out in the claims. It will be understood that the particular embodiments of the invention are shown by illustration and not as limitations of the invention. The principal features of the invention can be employed in various embodiments without departing from the scope of the present invention. All parts and percentages are by weight unless otherwise stated.

The present invention pertains to a method for treating photoablated corneal tissue. The method includes contacting photoablated corneal tissue with a biochemically engineered contact lens. The contact lens includes an amniotic composition such that scarring of the photoablated corneal tissue is reduced.

Photoablation of corneal tissue can be accomplished by excimer photorefractive keratectomy (PRK) for refractive correction of myopia, hyperopia, presbyopia and astigmatism. Photoablation of corneal tissue can also be accomplished by phototherapeutic keratectomy (PTK) for removal of anterior corneal opacities such as scarring after trauma or infection, or corneal dystrophies. A common problem associated with both PRK and PTK is the development of corneal haze/scarring of the photoablated corneal tissue. Corneal haze is the result of scarring after laser corneal ablation and is responsible for regression of the refractive correction and loss of best-corrected visual acuity after photoablative treatment.

The present invention also pertains to a method of conditioning a contact lens for treatment of photoablated corneal tissue. The method includes contacting the contact lens with an amniotic composition whereby the amniotic composition is deposited within the contact lens or on the surface of the contact lens. Suitable amniotic compositions include extracts from amniotic tissue and placental components.

The language "photoablated corneal tissue" is intended to cover that area of the cornea subjected to photoablative treatment, e.g. PRK or PTK, for reshaping of the surface of the cornea. Such photoablative treatment can be used for the correction of astigmatism myopia, hyperopia, presbyopia and for treating corneal pathology such as known to a person skilled in the art. Photoablation, generally, refers to the use of an intense beam of ultraviolet or infrared light having sufficient energy to cut into or through corneal tissue. Suitable sources of light include lasers, such as excimer lasers, infrared lasers, free-electron lasers with a wide range of ablative energy. The applied radiation is controlled in a manner such that desired reshaping of the cornea is obtained. The desired amount of correction is determined clinically based on refraction and a computer controlled laser delivery system to deliver the precise number of laser shots at predetermined locations on the cornea. The optical profile of the resulting corneal contours enables refocusing of images on the retina to achieve clear vision. For example, photorefractive keratectomy can be performed with a 193-μm excimer laser under topical anesthesia. A 193-μm excimer laser produces a beam with an energy of 180 mJ/cm$^2$ at a firing rate of 10 hertz. Each pulse ablates to a 0.25-μm depth of the corneal stroma. Commercial apparatus for photoablative surgery are art recognized and include for example Summit Technology's EXCIMED UV200 (Waltham, Mass.) and the VisX STAR (Santa Clara, Calif.).

The term "amniotic composition" is intended to include those materials which include biological growth factors found in amniotic membranes and amniotic fluid associated therewith. A preferred amniotic composition is an extract from amniotic membrane which is a biological membrane that lines the inner surface of the amniotic cavity and consists of a simple cuboidal epithelium, a thick basement membrane and an avascular mesenchymal layer containing hyaluronic acid. These amniotic compositions are obtained from amniotic tissue derived from mammals, such as pigs or humans. Amniotic membrane tissue is known to reduce inflammation, fibrovascular ingrowth, and to facilitate epithelialization in animal models (Smelser G K. Role of Epithelium in Incorporation of Sulfate in the Corneal Connective Tissue, in Duke-Elder S, Perkins, E S, eds. The Transparency of the Cornea, Oxford: Blackwell Scientific; 1960:125).

Amniotic membrane is believed to play an important role in the scarless wound healing process in a fetus (Streuli C H, Schmidhauser C, Kobrin M, Bissell M J and Derynck R. Extracellular Matrix Regulates Expression of the TGF-beta$_1$ Gene, J. Cell Biology, 1993; 120:253–260.). The mechanism by which the amniotic membrane modulates the wound healing process is believed to act through the basement membrane which facilitates epithelialization and/or through a biochemical effect of hyaluronic acid contained in the mesenchymal layer (Smelser et al., supra and Streuli et al., supra). It is believed that amniotic compositions, such as amniotic membrane, reduce inflammation and fibrovascular ingrowth by affecting fundamental molecular and cellular processes in wound healing such as cellular activation and apoptosis (Smelser et al., supra; Dunnington J H, Tissue responses in ocular wounds, Am J Ophthal 1957; 43:667; Streuli et al., supra; Shah M, Foreman D M, Ferguson M W J, Neutralization of TGF-beta$_1$ and TGF-beta$_2$ or exogenous addition of TGF-beta$_3$ to cutaneous rad wounds reduces scarring, J of Cell Science, 1995; 108:985–1002).

Amniotic compositions include cytokines, e.g., growth factors necessary for tissue development. The term "cytokine" includes but is not limited to growth factors, interleukins, interferons and colony stimulating factors. These factors are present in normal tissue at different stages of tissue development, marked by cell division, morphogenesis and differentiation. Among these factors are stimulatory molecules that provide the signals needed for in vivo tissue repair, e.g. growth factors. These cytokines can stimulate repair of the photoablated tissue.

Growth factors necessary for cell growth, e.g., rejuvination of corneal tissue, found within an amniotic composition are contacted with the photoablated corneal tissue. The amniotic composition includes proteins, e.g., collagen and elastin, glycoproteins, proteoglycans and glycosaminoglycans, such as hyaluronic acid. The growth factors, produced and secreted by amniotic cells, bind to the amniotic matrix and regulate cell behavior in a number of ways. These factors include, but are not limited to, epidermal growth factor, fibroblast growth factor (basic and acidic), nerve growth-factor, mast cell-stimulating factor and Schwann cell growth factor. Adams et al., "Regulation of Development and Differentiation by the Extracellular Matrix" *Development* Vol. 117, p. 1183–1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") describe matrix components that regulate differentiation and development. Further, Adams et al. disclose examples of association of growth factors with extracellular matrix proteins and that the extracellular matrix is an important part of the micro-environment and, in collaboration with growth factors, plays a central role in regulating differentiation and development. The teachings of Adams et al. and Kreis et al. are incorporated herein by reference.

The term "hyaluronic acid" is intended to include those polyanionic glycoaminoglycans affecting cellular activation and differentiation.

The term "contact lens" is art recognized and is intended to include those devices generally used for correction of visual acuity, for cosmetic purposes and for protection of the cornea, e.g., a device which does not correct for visual acuity. Contact lenses include those which are considered "hard", e.g., polymethylmethacrylate, which has excellent biocompatibility but has poor oxygen permeability, "rigid gas permeable", e.g., polysiliconemethacrylates which have excellent biocompatability and allow diffusion of oxygen through the polymeric structure and "soft", e.g., polyhydroxyethylmethacrylates which have excellent biocompatibility and also allow diffusion of oxygen through the polymeric structure by aqueous transport. Examples of materials used in contact lenses include polymethylmethacrylate, polysiliconeacrylates, polysiliconemethacrylates, polyfluoroacrylates, polyfluoromethacrylates, polyflurosiliconeacrylates, polysiliconemethacrylates, polymethacrylates, polyacrylates, polyurethanes, polysiliconeurethanes, or polyitaconates, and combinations thereof. These polymeric materials can also be crosslinked.

In one embodiment, a contact lens includes an amniotic composition in the form of a membrane or a film attached to the surface of the contact lens, preferably on the surface of the lens which is in contact with the photoablated corneal tissue. By "attached" in this context, reference is made not only to covalent bonding of amniotic membrane molecules to the contact lens surface but also to attractive interactions caused by such forces as hydrogen bonding, ionic bonding, bonding through Van der Waals forces and the like. For example, an amniotic composition can be covalently attached to the surface of a contact lens by the method taught in U.S. Pat. No. 4,973,493, the teachings of which are incorporated herein by reference.

The term "membrane" is art recognized and is intended to include those materials having a pore structure within the biological matrix. In general, a membrane has a pore size of between about 0.02 microns to about 2 microns and a thickness of between about 0.001 mm and about 0.1 mm. Preferably, amniotic membranes useful in this invention consist of three layers; the epithelium, basement membrane and stroma, the combination of which having a total thickness of between about 50 $\mu$m to about 100 $\mu$m.

The term "film" is also art recognized and is intended to include a continuous coating of the contact lens surface substantially devoid of pore structure throughout the film matrix. In general, the film has a thickness of between about 0.001 mm and about 0.1 mm. Preferably, the film has thickness of about 0.05 to about 0.5 mm.

Alternatively, the contact lens surface can have an amniotic composition which is a discontinuous layer. By the term "discontinuous" it is meant that discrete particles are attached to the contact lens surface. Preferably, at least about 50 percent of the contact lens surface area, which is in contact with the photoablated corneal tissue, has amniotic composition particulates. More preferably, at least about 75 percent of the contact lens surface has amniotic composition particulates, more preferably at least about 90 percent of the contact lens surface has particulates. In a most preferred embodiment, between about 95 and 99 percent of the contact lens surface area, which is in contact with the photoablated corneal tissue, has amniotic composition particulates.

The amniotic composition particulates range in size from between about 0.2 microns to about 10 microns. Preferably, the particulates range in size from between about 0.5 microns to about 5 microns. The particulates can be of varying sizes and dimensions, e.g. round, oblong, disc like. Furthermore, the particulates can be porous.

In another embodiment, the contact lens which is in contact with photoablated corneal tissue includes an amniotic composition which is entrapped within the contact lens. Therefore, the necessary tissue growth factors diffuse from within the contact lens, thereby stimulating healing of the photoablated corneal tissue.

In a preferred embodiment, the contact lenses of the invention which have either an amniotic membrane, film, or particulates attached to the surface of the contact lens, or which have the amniotic composition entrapped within the contact lens are periodically treated with a solution including an amniotic composition. For example, daily treatment of the contact lenses with a solution including an amniotic composition provides for incorporation of additional growth and tissue repair factors in the membrane, film, particulate or within the contact lens. The contact lens having the amniotic composition can be soaked in the solution for between about 1 to 12 hours; often overnight while the individual is sleeping.

Conditioning of the contact lens with solutions which contain amniotic compositions can be utilized to replenish or to increase growth and tissue repair factors as required. Typical concentrations of the amniotic composition in the solution are between about 2 percent and about 20 percent, preferably between about 5 percent and about 10 percent. Further, the solution can also include antibiotics such as amino glycosides, preferably tobramycin (O-3-amino-3-deoxy-α-D-glycopyranosyl-(1→4)-O-[2,6-diamino-2,3,6-trideoxy-α-D-ribo-hexopyranosyl-(1→6)]-2-deoxy-L-streptamine) to prevent infection during corneal tissue healing. Typical concentrations of the antibiotic(s) is in a range of between about 2 percent and about 20 percent, preferably between about 5 percent and about 10 percent.

The contents of all references, pending patent applications and published patent applications, cited throughout this application are hereby incorporated by reference.

EXEMPLIFICATION

Example 1

Preparation of Amniotic Membrane

Preparation of preserved human amniotic membrane is as follows (Smelser, et al., supra and Dunnington, supra.). Human placentas which passed routine screening for infections were obtained immediately after elective cesarean sections with normal gestations. The amniotic membrane was obtained from the placenta through blunt dissection and phosphate buffered saline (PBS) containing penicillin (1,000 U/ml), streptomycin (20 mg/ml) and amphotericin B (2.5 ug/ml). The amniotic membranes were washed several times with the PBS solution and were then layered onto a nitrocellulose membrane so that the mesenchymal side of the amniotic membrane was facing the filter forming a dual membrane. Additional washes of the dual membrane were performed using the PBS solution described above. The dual membrane was cut into 9 mm diameter circles and stored in 100% glycerin at 4° C.

Example 2

Application of Amniotic Membrane to a Contact Lens

The amniotic membrane of Example 1 can be used in the following example. A contact lens, e.g. Vistamarc or Lidofilcon can be contacted with the dual membrane and treated with sufficient pressure to cause the dual membrane to become attached to the inner surface of the contact lens. Alternatively, the dual membrane can be separated into its individual components. The amniotic membrane can be attached to be inner surface of the contact lens by application of sufficient pressure.

Example 3

Attachment of Amniotic Membrane or Particles to a Contact Lens

The amniotic membrane is prepared as in Example 1 without the use of the nitrocellulose as a support. The pretreated amniotic membrane can be contacted with a contact lens treated with a coupling agent as described in U.S. Pat. No. 4,973,493 to effect attachment of the amniotic membrane to the contact lens surface.

Alternatively, the amniotic membrane can be treated under shearing conditions, such as blenderizing, to effect a particle size of between about 0.01 microns and 5 microns. The particulates, suspended in solution, can be contacted with a pretreated contact lens, as described above, to effect attachment of the amniotic particulates to the contact lens surface.

Example 4

Attachment of Amniotic Film to a Contact Lens

The particulates as described in Example 3 can be dissolved in a solvent and/or a binding agent and coated unto a contact lens. The coated lens is then dried, leaving an amniotic film deposited onto the contact lens surface. This process can be performed several times to effect the degree of coating desired.

Example 5

Preparation of a Contact Lens with Amniotic Membrane Entrapped Therein

The amniotic membrane of Example 1 without the nitrocellulose support is blenderized in a solvent, such as ethylene glycol. A mixture of 60 grams methyl methacrylate, 20 grams of N-vinylpyrrolidone, 10 grams neopentyl glycol dimethacrylate, 20 grams of dineopentyl fumarate and 2 grams of the (1 percent solids) blenderized amniotic membrane can be treated with 0.06 grams of Vaso 52 initiator, an azo initiator (E. I. DuPont deNemours of Wilmington, Del.). The mixture can be stirred at room temperature for one hour, filtered into silylated glass test tubes and purged with nitrogen prior to heating at 40° C. for 48 hours, 65° C. for 24 hours and 75° C. for 24 hours. The resultant polymeric material can be cut into contact lenses by methods known to those skilled in the art. The contact lens material which contains the amniotic membrane can be extracted with water prior to cutting and lathing or after such steps to remove residual ethylene glycol.

Example 6

Treatment of a Contact Lens with an Amniotic Solution

The contact lens described in Examples 2–5 can be further treated with an aqueous solution which contains an amniotic composition. The solution of amniotic composition can be formed by blenderizing the amniotic membrane (without the nitrocellulose backing) of Example 1 to a particle size between about 0.01 microns and 5.0 microns. The concentration of the amniotic composition in the solution is between about 10 and 30 weight percent. The contact lens can be immersed in the aqueous solution for a period of time sufficient to allow tissue repair and growth factors to become entrapped within the contact lens and/or attached to the amniotic membrane, film or particulates on the contact lens surface. Typically, the contact lens is contacted with the solution for a period of about 8 hours and can be repeated on a daily basis.

Alternatively, a contact lens not previously treated with an amniotic composition can be treated with the amniotic solution. The contact lens can be immersed in the solution for a period of time sufficient to allow tissue repair and growth factors to become attached to the contact lens surface and/or entrapped within the contact lens. Typically, the untreated contact lens is placed in the solution for a period of about 8 hours and can be repeated on a daily basis.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for treating photoablated corneal tissue, comprising contacting photoablated corneal tissue with a contact lens which includes an amniotic composition such that scarring of the photoablated corneal tissue is reduced.

2. The method of claim 1, wherein said contact lens is formed from polymethylmethacrylate, polysiliconeacrylates, polysiliconemethacrylates, polyfluoroacrylates, polyfluoromethacrylates, polyflurosiliconeacrylates, polysiliconemethacrylates, polymethacrylates, polyacrylates, polyurethanes, polysiliconeurethanes, or polyitaconates, and combinations thereof.

3. The method of claim 1, wherein said amniotic composition is a biochemical extract from amniotic membrane attached to the surface of said contact lens which is in contact with said photoablated corneal tissue.

4. The method of claim 1, wherein said amniotic composition is entrapped within said contact lens, such that said amniotic composition is released over time to said photoablated corneal tissue.

5. The method of claim 1, wherein said amniotic composition is a film attached to the surface of said contact lens which is in contact with said photoablated corneal tissue.

6. The method of claim 1, wherein said amniotic composition comprises tissue repair factors.

7. The method of claim 6, wherein said tissue repair factors include factors necessary for cell division, differentiation and tissue morphogenesis.

8. A method for conditioning a contact lens for treatment of photoablated corneal tissue, comprising contacting said contact lens with an amniotic composition whereby said amniotic composition is deposited in or on the surface of said contact lens.

9. The method of claim 8, wherein said contact lens is formed from polymethylmethacrylate, polysiliconeacrylates, polysiliconemethacrylates, polyfluoroacrylates, polyfluoromethacrylates, polyflurosiliconeacrylates, polysiliconemethacrylates, polymethacrylates, polyacrylates, polyurethanes, polysiliconeurethanes, or polyitaconates, and combinations thereof.

10. The method of claim 8, wherein said amniotic composition is an amniotic membrane attached to the surface of said contact lens.

11. The method of claim 8, wherein said amniotic composition is entrapped within said contact lens.

12. The method of claim 8, wherein said amniotic composition is a film comprising amniotic tissue and a binder attached to the surface of said contact lens.

13. The method of claim 8, wherein said amniotic composition comprises tissue repair factors.

14. The method of claim 13, wherein said tissue repair factors include factors necessary for cell division, differentiation and tissue morphogenesis.

* * * * *